United States Patent [19]
Fink et al.

[11] Patent Number: 5,668,154
[45] Date of Patent: Sep. 16, 1997

[54] PYRIDINIMINYL-1,2-BENZISOXAZOLES AND -BENZISOTHIAZOLES

[75] Inventors: David M. Fink, Lebanon, N.J.;
Barbara E. Kurys, Loveland, Ohio;
Gregory M. Shutske, Pittstown, N.J.;
John D. Tomer, IV, Perkasie, Pa.

[73] Assignee: Hoechst Marion Roussel Inc., Cincinnati, Ohio

[21] Appl. No.: 637,091

[22] Filed: May 2, 1996

Related U.S. Application Data

[63] Continuation-in-part of Ser. No. 466,021, Jun. 6, 1995, abandoned.
[51] Int. Cl.$^6$ .......................... A61K 31/44; C07D 401/12
[52] U.S. Cl. .......................... 514/338; 514/342; 514/340; 546/272.1; 546/271.1
[58] Field of Search .................. 514/340, 338, 514/342; 546/272.1, 271.1

[56] References Cited

U.S. PATENT DOCUMENTS 5,494,908  2/1996  O'Malley et al. .................. 544/62

FOREIGN PATENT DOCUMENTS 0509402  10/1992  European Pat. Off. .
0594000  4/1994  European Pat. Off. .

*Primary Examiner*—Jane Fan
*Attorney, Agent, or Firm*—Nelsen L. Lentz

[57] ABSTRACT

Novel pyridiniminyl-1,2-benzisoxazoles and -benzisothiazoles, intermediates and processes for the preparation thereof, and methods of relieving memory dysfunction and treating depression utilizing the 1,2-benzisoxazoles and -benzisothiazoles and intermediates, or compositions thereof are disclosed.

44 Claims, No Drawings

PYRIDINIMINYL-1,2-BENZISOXAZOLES AND -BENZISOTHIAZOLES

This is a continuation-in-part application of Ser. No. 08/466,021, filed Jun. 6, 1995 now abandoned.

The present invention relates to 1,2-benzisoxazoles and -benzisothiazoles. More particularly, the present invention relates to pyridiniminyl-1,2-benzisoxazoles and -benzisothiazoles of formula 1

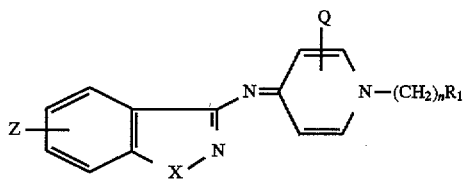

wherein $R_1$ is hydrogen, loweralkyl, loweralkenyl, loweralkynyl, lowercycloalkyl, —C(=O)O-loweralkyl, 1,3-dioxolane, phenyl, cinnamyl, phenyl substituted by loweralkyl, loweralkoxy, halogen, hydroxyl, nitro or trifluoromethyl; Q is hydrogen, halogen, loweralkyl or nitro; X is oxygen or sulfur; Z is hydrogen, loweralkyl, loweralkoxy, hydroxyl, halogen, nitro, or trifluoromethyl; n is 1 to 12; the geometric isomers, the optical isomers, or the pharmaceutically acceptable salts thereof, useful in relieving memory dysfunction and thus indicated in the treatment of Alzheimer's disease, as well as in the treatment of depression.

Subgeneric to the compounds of formula 1 are those wherein X is oxygen and $R_1$ is hydrogen or loweralkyl; and those wherein X is oxygen and $R_1$ is phenyl or phenyl substituted by loweralkyl, loweralkoxy, halogen, hydroxyl, nitro, or trifluoromethyl.

The present invention further relates to pyridinylamino-1,2-benzisoxazoles and -benzisothiazoles of formula 2

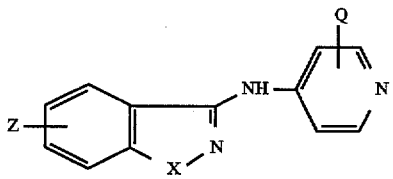

wherein Q is hydrogen, halogen, loweralkyl or nitro; X is oxygen or sulfur; Z is hydrogen, loweralkyl, loweralkoxy, hydroxyl, halogen, nitro, or trifluoromethyl; the optical isomers, or pharmaceutically acceptable salts thereof, useful as intermediates for the preparation of the pyridiniminyl-1,2-benzisoxazoles and -benzisothiazoles of formula 1, and also for the relief of memory dysfunction and treatment of depression.

Unless otherwise noted, the following terms have the given definitions. As used throughout the specification and appended claims, the term "alkyl" refers to a straight or branched chain hydrocarbon radical containing no saturation and having 1 to 8 carbon atoms. Examples of alkyl groups are methyl, ethyl, 1-propyl, 2-propyl, 1-butyl, 1-hexyl, 3-hexyl, 4-heptyl, 2-octyl and the like. The term "alkoxy" refers to a monovalent substituent which consists of an alkyl group linked through an ether oxygen having its free valence bond from the ether oxygen. Examples of alkoxy groups are methoxy, ethoxy, propoxy, 1-butoxy, 1-pentoxy, 3-hexoxy, 4-heptoxy, 2-octoxy and the like. The term "alkenyl" refers to a straight or branched chain hydrocarbon radical containing unsaturation in the form of a single carbon to carbon double bond and having from 3 to 7 carbon atoms such as propenyl, 2-butenyl, 3-ethyl-2-pentenyl, and the like; the term "alkynyl" refers to a straight or branched chain hydrocarbon radical containing unsaturation in the form of a single carbon to carbon triple bond and having from 3 to 7 carbon atoms such as 2-propynyl, 2-butynyl, 1-methyl-2-butynyl, 4-methyl-2-pentynyl, 4,4-dimethyl-2-butynyl and the like; the term "cycloalkyl" refers to a saturated hydrocarbon group possessing at least one carbocyclic ring, the ring containing from 3 to 10 carbon atoms such as cyclopropyl, cyclobutyl, cyclopentyl, cyclohexyl, cyclooctyl, 1-adamantyl and the like. The term "alkanol" refers to a compound formed by a combination of an alkyl group and hydroxy radical. Examples of alkanols are methanol, ethanol, 1- and 2-propanol, 2,2-dimethylethanol, hexanol, octanol and the like. The terms "halogen", "Hal" or "halo" refers to a member of the family fluorine, chlorine, bromine, or iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, or by synthesis from optically active precursors.

The present invention comprehends all optical isomers and racemic forms thereof of the compounds disclosed and claimed herein and the formulas of the compounds shown herein are intended to encompass all possible optical isomers of the compounds so depicted. In addition, the patent application entitled "PYRIDINIMINYL-1,2-BENZISOXAZOLES AND -BENZISOTHIAZOLES", U.S. Ser. No. 08/466,021, filed Jun. 6, 1995, is incorporated herein by reference.

The novel pyridiniminyl-1,2-benzisoxazoles can be prepared following steps A, A' and B as set forth in the Reaction Scheme. The-benzisothiazoles of the present invention can be prepared following steps A and B as set forth in the Reaction Scheme.

As described in the Reaction Scheme, steps A and B, to prepare a pyridiniminyl-1,2-benzisoxazole of formula 1, wherein X is oxygen, for example, a pyridiniminyl-1,2-benzisoxazole 1, an aminobenzisoxazole 3 is condensed with a halopyridine of formula 5

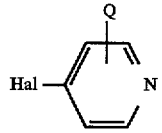

wherein Hal is chloro or bromo and Q is as above to yield a pyridinylamino-1,2-benzisoxazole 2 wherein X, Q, and Z are as above, which, in turn, is alkylated with an alkyl halide of formula 6

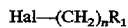

wherein Hal is chloro or bromo and $R_1$ and n are as above to yield an ultimate pyridiniminylbenzisoxazole 1 wherein $R_1$, Q, X, Z, and n are as above.

The condensation of amine 3 with halopyridine 5 is generally performed in a polar aprotic solvent, for example, N-methylpyrrolidinone, dimethylacetamide, dimethylformamide, hexamethylphosphoramide, or dimethylsulfoxide. While the condensation temperature is not narrowly critical, elevated temperatures in the range of about 100° to about 150° C. may be employed to facilitate the reaction, depending on the reaction solvents. A condensation temperature of about 130° C. is preferred.

The alkylation is conveniently carried out in an inert solvent such as acetonitrile at the reflux temperature of the reaction medium. The alkylation may be performed at reduced temperatures, for example, within the range of from about ambient temperature to approaching about the reflux temperature of the medium.

Alternatively, the alkylation may be achieved in an inert solvent such as an aprotic dipolar solvent (dimethylacetamide, dimethylsulfoxide, hexamethylphosphoramide and the like) in the presence of a base such as, for example, an alkali metal hydride, namely lithium, sodium or potassium hydride, sodium hydride being preferred. The alkylation temperature may vary from about ambient to about 80° C. An alkylation temperature of about 60° C. is preferred.

The starting 3-amino-1,2-benzisoxazole 3, for example, an aminobenzisoxazole 3, wherein X is oxygen and Z is as above is commercially available or preparable by the process described in G. M. Shutske and K. J. Kapples, Journal of Heterocyclic Chemistry, 26, 1293 (1989). In addition, the starting 3-amino- 1,2-benzisothiazoles are readily prepared by one of ordinary skill in the art, for example, following the procedures as disclosed by Rahman and Scrowston, *J. Chem. Soc. Perkin Trans. I,* 2973 (1983) and 385 (1984).

As described in the Reaction Scheme, steps A' and B, the intermediate 3-pyridinylamino-1,2-benzisoxazole 2, for example, a pyridinylamino benzisoxazole 2 wherein X is oxygen and Q and Z are as above, in the alternative, may be prepared by treating a 2-fluoro or 2-nitro-N-4-pyridinylbenzamide 7 with thionyl chloride followed by treating the imidoylchloride, so obtained, generally without purification, with O-trimethylsilylhydroxyl amine, to afford an amidoxime, and treating the amidoxime, also without purification, with a base to yield a pyridinyl-1,2-benzisoxazole 2. Specifically, 2,5-difluoro-N-pyridinylbenzamide 7, wherein Q is hydrogen and Z is 5-fluoro is treated with thionyl chloride in the presence or absence of a solvent (1,1-dichloroethane) at the reflux temperature of the reaction medium to provide 2,5-difluorophenyl-N-(1H)-pyridinimidoyl chloride which, in turn, is treated with O-trimethylsilylhydroxyl amine in an ethereal solvent such as tetrahydrofuran at ambient temperature to give 2,5-difluoro-4-(pyridinylamino)methanone oxime and the latter with an alkali metal alkoxide such as potassium t-butoxide in an ethereal or dipolar aprotic solvent such as tetrahydrofuran or dimethylformamide, respectively, at an elevated temperature to yield 5-fluoro-3-[4-(pyridinyl) amino]-1,2-benzisoxazole.

One of ordinary skill in the art would readily recognize that the corresponding 1,2-benzisothiazoles of the present invention are prepared in a manner analogous to the procedure described in the Reaction Scheme, steps A and B as set forth above for preparing the 1,2-benzisoxazoles 2 and 3.

The pyridiniminyl-1,2-benzisoxazoles and -benzisothiazoles and related compounds of the present invention are useful as agents for the relief of memory dysfunction, particularly dysfunctions associated with decreased cholinergic activity such as those found in Alzheimer's disease. Relief of memory dysfunction activity is demonstrated in the in vitro inhibition of acetylcholinesterase assay, an assay for the determination of the ability of a drug to inhibit the inactivation of acetylcholine, a neurotransmitter implicated in the etiology of memory dysfunction and Alzheimer's dementia. In this assay, a modification of a test described by G. L. Ellman, et al., Biochemical Pharmacology, 7, 88 (1961 ), the following reagents are prepared and employed:

1. 0.05M Phosphate Buffer (pH 7.2)

A solution of monobasic sodium phosphate monohydrate (6.85 g) in distilled water (100 mL) is added to a solution of dibasic sodium phosphate heptahydrate (13.4 g) and distilled water (100 mL) until a pH of 7.2 was attained. The solution was diluted 1 to 10 with distilled water.

2. Substrate in Buffer

The 0.05M Phosphate Buffer (pH 7.2) was added to acetylthiocholine (I 98 mg) to a total volume of 100 mL, i.e., a quantity sufficient (gs) to 100 mL.

3. 5,5-Dithiobisnitrobenzoic acid in Buffer

The 0.05M Phosphate Buffer (pH 7.2) was added to 5.5-dithiobisnitrobenzoic acid to a total volume of 100 mL. i.e., a quantity sufficient (gs) to 100 mL.

4. Stock Solution of Drug

A 2 millimolar stock solution of the test drug is prepared in a quantity sufficient of either acetic acid or dimethyl sulfoxide to volume with 5,5-Dithiobisnitrobenzene Acid in Buffer. Stock Solution of Drug is serially diluted (1:10) so that the final cuvette concentration is $10^{-4}$ molar.

Male Wistar rats are decapitated, brains rapidly removed, corpora striata dissected free, weighted and homogenized in 19 volumes (approximately 7 mg protein/mL) of 0.05M phosphate Buffer (pH 7.2) using a Potter-Elvehjem homogenizer. A 25 µl aliquot of this suspension is added to 1 mL of the vehicle or various concentrations of the test drug and preincubated for 10 minutes at 37° C. Enzyme activity is measured with a Beckman DU-50 spectrophotometer with the following software and instrument settings:

1. Kinetics Soft-Pac® Module #598273;
2. Program #6 Kindata;
3. Source—Vis;
4. Wavelength —412 nm;
5. Sipper—none;
6. Cuvettes—2 mL cuvettes using auto 6-sampler;
7. Blank—1 for each substrate concentration;
8. Interval time—15 seconds (15 or 30 seconds for kinetics);
9. Total time—5 minutes (5 to 10 minutes for kinetics);
10. Plot—yes;
11. Span—autoscale;
12. Slope—increasing;
13. Results—yes (gives slope); and
14. Factor—1.

Reagents are added to the blank and sample cuvettes as follows:

1. Blank: 0.8 mL 5.5-Dithiobisnitrobenzoic Acid 0.8 mL Substrate in Buffer
2. Control: 0.8 mL 5.5-Dithiobisnitrobenozic Acid/ Enzyme 0.8 mL Substrate in Buffer
3. Drug: 0.8 mL 5.5-Dithiobisnitrobenzoic Acid/Drug/ Enzyme 0.8 mL Substrate in Buffer Blank values are determined for each run to control for non-enzymatic hydrolysis of substrate and these values am automatically subtracted by the Kindata program available on kinetics soft-pac module. This program also calculates the rate of absorbance change for each cuvette.

For $IC_{50}$ Determinations

Substrate concentration is 10 millimolar diluted 1:2 in assay yielding final concentration of 5 millimolar. 5,5-Dithiobisnitrobenzoic acid concentration is 0.5 millimolar yielding 0.25 millimolar final concentration.

$$\% \text{ Inhibition} = \frac{\text{Slope Control} - \text{Slope drug}}{\text{Slope Control}} \times 100$$

$IC_{50}$ values are calculated from log-probit analysis

TABLE I

| Compound | Inhibition of Acetylcholinesterase Activity $IC_{50}(\mu M)$ |
|---|---|
| 3-[1-phenylmethyl-N-4(1H)-pyridiniminyl]-1,2-benzisoxazole | 0.28 |
| 3-[1-phenylpropyl-N-4(1H)-pyridiniminyl]-1,2-benzisoxazole | 0.65 |
| 6-Methoxy-3-[1-phenylmethyl-N-4(1H)-pyridiniminyl]-1,2-benzisoxazole | 0.09 |
| 3-[1-(4-fluoraphenyl)methyl-N-4(1H)-pyridiniminyl]-1,2-benzisoxazole | 0.44 |
| tacrine | 0.32 |

Relief of memory dysfunction is achieved when the present pyridiniminyl-1,2-benzisoxazoles and -benzisothiazoles and related compounds are administered to a subject requiring such treatment as an effective oral, parenteral or intravenous dose of from 0.10 to 50 mg/kg of body weight per day. A particularly effective amount is about 10 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The pyridiniminyl-1,2-benzisoxazoles and -benzisothiazoles of the present invention are also useful as agents for treating depression. Depression treatment is demonstrated in the in vitro inhibition of monoamine oxidase assay, an assay for the determination of the ability of a drug to inhibit the enzyme monoamine oxidase. In this assay, a modification of an assay described by M. V. Kindt, et al., Europ. J. Pharmacol. 146: 313–318 1988.

The following reagents are prepared:

1. Phosphate buffer (0.5M), pH 7.4; 134.4 g dibasic sodium phosphate heptahydrate q.s. to 1 liter in distilled water (A) 17.3 g monobasic sodium phosphate q.s. to 250 mL in distilled water (B) Adjust pH of A to 7.4 by slowly adding B (volumes as needed) Dilute 1:10 in distilled water (0.05M phosphate buffer, pH 7.4)
2. 0.25M Sucrose (phosphate buffered): 21.4 g sucrose, q.s. to 250 mL with 0.05M phosphate buffer
3. Substrate for monoamine oxidase-A:
   a. serotonin creatine sulphate (5-hydroxytryptamine) is obtained
   from Sigma Chemical Company. A 5 mM stock solution is made up in 0.01 N-hydrochloride. The solution is used to dilute the specific activity of the [$^3$H]-hydroxytryptamine.
   b. [$^3$H]-5-Hydroxytryptamine binoxalate (20–30 Ci/mmol) is obtained from New England Nuclear.
   c. Add 12 μl of [$^3$H]-5-hydroxytryptamine to 2 mL of the 5 mN 5-hydroxytryptamine solution. (Final amine concentration in the assay is 200 μM: see below.)
4. Substrate for monoamine oxidase-B
   a. -phenethylamine is obtained from Sigma Chemical Company. A 5 mM stock solution is made up in 0.01 N-hydrochloride. The solution is used to dilute the specific activity of the [$^{14}$C]-phenethylamine.
   b. -[ethyl-1-$^{14}$C]-phenethylamine hydrochloride (40–50 mCi/mmol) is obtained from New England Nuclear.
   c. Add 12 μl of [$^{14}$C]-phenethylamine to 2 mL of the 5 mM -phenethylamine solution. (Final amine concentration in the assay is 200 μM: see below.)
5. Equal amounts of monoamine oxidase-A (5-hydroxytryptamine) and monoamine oxidase-B (-phenethylamine) substrates are combined for simultaneously testing both monoamine oxidase types, i.e., mixed stock solution of 2.5 mN 5-hydroxytryptamine and 2.5 mM -phenethylamine, 40 μl of this mixed solution gives a 200 μM final concentration of each amine in the assay. When testing only one monoamine oxidase type, the individual 5 mM stock solutions must be diluted 1:1 with distilled water prior to adding 40 μl to the incubation mixture; i.e., same 200 μM final amine concentration.
6. Stock solutions of test drugs am made up in appropriate vehicles and serially diluted to give final concentrations ranging from $10^7$ to $10^{-3}$ molar in the assay. Lower concentrations can be made for more potent drugs.

Tissue Preparation

Male Wistar rats weighing 150–250 grams were sacrificed and the brains rapidly removed. Whole brain minus cerebellum was homogenized in 30 volumes of ice-cold, phosphate-buffered 0.25M sucrose, using a Potter-Elvejhem homogenizer. The homogenate was centrifuged at 1000 g for 10 minutes and the supernatant ($S_1$) decanted and recentrifuged at 18,000 g for 20 minutes. The resulting pellet ($P_2$) was resuspended in fresh 0.25M sucrose and serves as the tissue source for mitochondrial monoamine oxidase.

C. Assay

10 μl 0.5M phosphate buffer, pH 7.4

50 μl water or appropriate drug concentration

400 μl Tissue suspension

Tubes are preincubated for 15 minutes at 37° C. and the assay is started by adding 40 μl of combined substrate ([$^3$H]-5-hydroxytryptamine and [$^{14}$C]-phenethylamine) at 15 second intervals. The tubes are incubated for 30 minutes at 37° C. and the reaction stopped by the addition of 0.3 mL 2N-hydrochloric acid. Tissue blank values are determined by adding the acid before the radioactive substrate. The oxidative products of the reaction are extracted with ethyl acetate/toluene (1:1). Add 5 mL of this mixture to the tubes, vortex for 15 seconds to extract the deaminated metabolites into the organic phase and allow to separate from the aqueous phase. Place tubes in acetone/dry ice bath to freeze the aqueous layer. When this layer is frozen, pour off the top organic layer into a scintillation vial. Add 10 mL Liquiscint and count the samples using window settings for $^{14}$C in one channel and $^3$H in the second channel. $IC_{50}$ values are determined by log-probit analysis.

Results

TABLE II

| Compound | Monoamine Oxidase A IC50 (μM) | Monoamine Oxidase B |
|---|---|---|
| 6-Chloro-3-[1-propyl-N-4(1H)pyridiniminyl-1,2-benzisoxazole | 1.65 | 27.2 |
| 3-[1-phenylmethyl-N-4(1H)-pyridiniminyl]-1,2-benzisoxazole | 9.0 | 33.7 |
| 3-[1-(2-phenylethyl)-N-4(1H)-pyridiniminyl]-1,2-benzisoxazole | 3.0 | 15.9 |
| 6-Methoxy-3-[1-phenylmethyl-N-4(1H)-pyridiniminyl]-1,2-benzisoxazole | 3.0 | 25.2 |
| brofaromine | 0.18 | 23.4 |

Depression treatment is achieved when the present pyridiniminyl-1,2-benzisoxazoles or -benzisothiazoles and related compounds are administered to a subject requiring such treatment as an effective oral, parenteral or intravenous dose of from 0.10 to 50 mg/kg of body weight per day. A particularly effective amount is about 10 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Acetylcholinesterase inhibitors and monoamine oxidase inhibitors are known in the art as being useful as relievers of memory dysfunction and antidepressants, respectively. (See V. Kumar in Alzheimer's Disease: Therapeutic Strategies, E. Giacobini and R. Becker Eds.; Birkhauser, Boston 1994 for memory dysfunction utility and K. F. Tipton in Biochemical and Pharmacological Aspects of Depression, K. F. Tipton and U.B.H. Youdin, Eds., Taylor and Francis, London 1989 for antidepressant utility. It is understood by one of ordinary skill in the art that humans, mice, rats and the like are included within the scope of the term "mammal".

Effective amounts of the compounds of the invention may be administered to a subject by any one of various methods, for example, orally as in capsules or tables, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tables. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compounds, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mg of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterores; a glidant such as colloidal silicon dioxide; and a sweetening agent such as sucrose or saccharin or a flavoring agent such as peppermint, methyl, salicylate, or orange flavoring may be added. When the dosage unit is a capsule it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mg of the active compound.

The solutions or suspensions may also include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in ampules, disposable syringes or multiple vials made of glass or plastic.

Compounds of the invention include:

a. 6-methyl-3-[1-propyl-N-4(1H)pyridiniminyl]-1,2-benzisoxazole;

b. 5-hydroxy-3-[1-methyl-N-4(1H)pyridiniminyl]-1,2-benzisoxazole;

c. 3-[1-ethyl-N-4(1H)pyridiniminyl]-5-trifluoromethyl-1,2-benzisoxazole;
d. 3-[1-(2-propenyl)-N-4(1H)pyridiniminyl]-1,2-benzisoxazole;
e. 3-[1-(2-propynyl)-N-4(1H)pyridiniminyl]-1,2-benzisoxazole;
f. 3-[1-cyclohexyl-N-4(1H)pyridiniminyl]-1,2-benzisoxazole;
g. 3-[1-(4-hydroxyphenylmethyl-N-4(1H)pyridiniminyl]-1,2-benzisoxazole;
h. 3-[1-propyl-N-4(1H)pyridiniminyl]-1,2-benzisothiazole;
i. 3-[1-propyl-N-[2-chloro-4(1H)pyridiniminyl]-1,2-benzisoxazole;
j. 3-[1-propyl-N-[2-methyl-4(1H)pyridiniminyl]-1,2-benzisoxazole;
k. 3-[1-propyl-N-[2-nitro-4(1H)pyridiniminyl]-1,2-benzisoxazole;
l. 3-[1-decyl-N-4(1H)pyridiniminyl]-1,2-benzisoxazole;
m. 5-methyl-3-(4-pyridinylamino)-1,2-benzisoxazole;
n. 6-hydroxy-3-(4-pyridinylamino)-1,2-benzisoxazole;
o. 7-nitro-3-(4-pyridinylamino)-1,2-benzisoxazole;
p. 3-(4-pyridinylamino-3-trifluoromethyl)-1,2-benzisoxazole;
q. 3-(2-chloro-4-pyridinylamino)-1,2-benzisoxazole;
r. 3-(2-methyl-4-pyridinylamino)-1,2-benzisoxazole;
s. 3-(2-nitro-4-pyridinylarnino)- 1,2-benzisoxazole; and
t. 3-(4-pyridinylamino)-1,2-benzisothiazole.

The following examples present typical syntheses as described in the Reaction Scheme. The reagents and starting materials are commercially available or are readily prepared by one of ordinary skill in the art. These examples are understood to be illustrative only and are not intended to limit the scope of the present invention in any way. As used herein, the following terms have the indicated meanings: "kg" refers to kilograms; "g" refers to grams; "mg" refers to milligrams; "gg" refers to micrograms; "ppm" refers to parts per million; "mmol" refers to millimoles; "mL" refers to milliliters; "cm" refers to centimeters; "L" refers to liters; "°C" refers to degrees Celsius; "mm Hg" refers to millimeters of mercury; "rpm" refers to revolutions per minute; "Rr" refers to retention factor; "bp" refers to boiling point; "top" refers to melting point; "dec" refers to decomposition; "$[\alpha]^D_{20}$" refers to specific rotation of the D line of sodium at 20° C. obtained in a 1 decimeter cell; "c" refers to concentration in g/mL; "TFA" refers to trifluoroacetic acid; "THF" refers to tetrahydrofuran, "DMF" refers to dimethylformamide, "M" refers to molar; "mM" refers to millimolar; "gM" refers to micromolar; "nM" refers to nanomolar; "µL" refers to microliters; "HPLC" refers to high performance liquid chromatography; "eq" refers to equivalents; "hr." refers to hours; "N" refers to normal; and "µCi" refers to microcuries.

EXAMPLE ONE

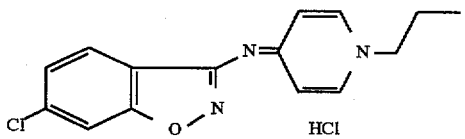

6-Chloro-3-[1-propyl-N-4(1H)pyridiniminyl]-1,2-benztsoxazole hydrochloride.

To a suspension of pentane washed sodium hydride (380 rag) in dimethylformamide (5 mL) was added 1-bromopropane (0.862 mL) followed by 6-chloro-3-(4-pyridyl)amino-1,2-benzisoxazole (2.33 g) in dimethylformamide (10 mL) dropwise. After stirring for 5 hr., an additional 0.3 mL of 1-bromopropane was added, and the reaction mixture was heated to 60° C. for one-half hr. The reaction mixture was cooled and distributed between diethyl ether and water. The precipitate was collected and washed with water and diethyl ether to yield 1.21 g of free base product. The free base was taken up in methanol/ethereal hydrogen chloride, and the solution was concentrated. The residue was triturated with diethyl ether and then recrystallized from methanol/diethyl ether to yield 992 mg (32%) of product from two crops, mp 278° C. (d), after drying under high vacuum, phosphorous pentoxide, and refluxing xylenes.

Analysis:

Calculated for $C_{15}H_{14}N_3OCl$—HCl: 55.57% C 0 4.66% H 12..96% N

Found: 55.39% C 3 4.55% H 12.97% N

EXAMPLE TWO

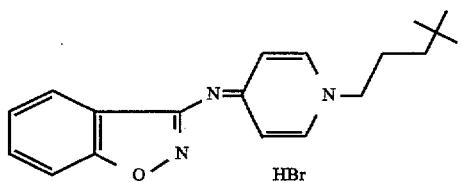

3-[1- (4,4-Dimethyl)pentyl-N-4(1H) -pyridiniminyl] -1,2-benzisoxazole hydrobromide.

A mixture of 3-[(4-pyridinyl)amino]-1,2-benzisoxazole (1.2 g) and 1-bromo-4-dimethyl-pentane (3.1 g) in acetonitrile (25 mL) was heated under reflux for 24 hr. The reaction mixture was allowed to cool to room temperature, and the precipitate was collected. The precipitate was washed with diethyl ether and dried in vacuo, to afford 0.60 g, (27%) of product. Two recrystallizations from isopropanol yielded the analytically pure sample, mp 236°–237° C.

Analysis:

Calculated for $C_{19}H_{24}BrN_3O$: 58.46% C 6.21% H 10.77% N

Found: 58.18% C 5.91% H 10.70% N

EXAMPLE THREE

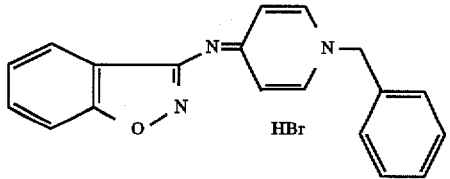

3-[1-Phenylmethyl-N-4(1H)-pyridiniminyl]-1,2-benztsoxazole hydrobromide.

A mixture of 3-[(4-pyridinyl)amino]-1,2-benzisoxazole (0.84 g) and benzyl bromide (0.68 g) in acetonitrile (20 mL) was heated under reflux for 1.5 hr. The reaction mixture was allowed to cool to room temperature, and the precipitate was collected. The precipitate was washed with diethyl ether and dried in vacuo, to afford 1.4 g (92%) of product, mp 285°–287° C.

Analysis:

Calculated for C$_{19}$H$_{16}$BrN$_3$O: 59.70% C 4.22% H 10.99% N

Found: 59.64% C 4.34% H 11.15% N

EXAMPLE FOUR

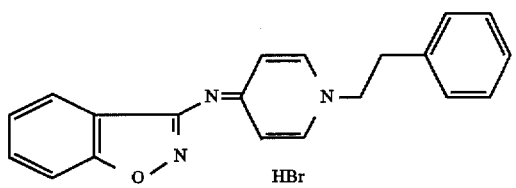

3-[1-(2-Phenylethyl)-N-4(1H)-pyrtdiniminyl]-1,2-benzisoxazole hydrobromide.

A mixture of 3-[(4-pyridinyl)amino]-1,2-benzisoxazole (1.0 g) and phenethyl bromide (0.87 g) in acetonitrile (19 mL) was heated under reflux for 10 hr. The reaction mixture was allowed to cool to room temperature, and the precipitate was collected. The precipitate was washed with diethyl ether and dried in vacuo to afford 1.0 g (54%) of product mp 259°–261 ° C.

Analysis:

Calculated for C$_{20}$H$_{18}$BrN$_3$O: 60.62% C 4.58% H 10.60% N

Found: 60.41% C 4.61% H 10.61% N

EXAMPLE FIVE

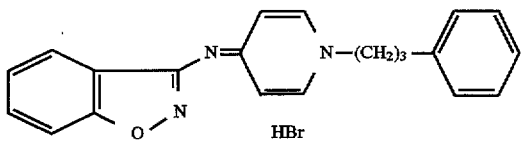

3-[1-(3-Phenylpropyl)-N-4(1H) -pyridiniminyl]-1,2-benzisoxazole hydrobromide.

A mixture of 3-[(4-pyridinyl)amino]-1,2-benzisoxazole (1.07 g) and 3-phenylpropyl bromide (1.51 g) in acetonitrile (25 mL) was heated under reflux for 24 hr. The mixture was allowed to cool to room temperature, and the precipitate was collected. The precipitate was washed with diethyl ether and dried in vacuo, to afford 1.27 g (61%) of product, mp 226°–227° C.

Analysis:

Calculated for C$_{21}$H$_{20}$BrN$_3$O: 61.47% C 4.91% H 10.24% N

Found: 61.37% C 5.11% H 10.15% N

EXAMPLE SIX

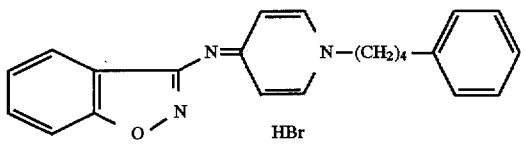

3-[1-(4-Phenylbutyl)-N-4(1H)-pyridiniminyl]-1,2-benzisoxazole hydrobomide.

A mixture of 3-[(4-pyridinyl)amino]-1,2-benzisoxazole (1.0 g) and 1-bromo-4-phenylbutane (1.0 g) in acetonitrile (25 mL) was heated under reflux for 24 hr. The mixture was allowed to cool to room temperature, and the precipitate was collected. The precipitate was washed with diethyl ether and dried in vacuo to afford 1.30 g (65%) of product, mp 207°–208° C.

Analysis:

Calculated for C$_{22}$H$_{22}$BrN$_3$O: 62.27% C 5.23% H 9.90% N

Found: 62.26% C 5.18% H 9.90% N

EXAMPLE SEVEN

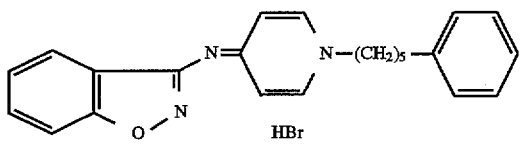

3-[1-(5-Phenylpentyl-N-4(1H)-pyridiniminyl]-1,2-benzisoxazole hydrobromlde.

A mixture of 3-[(4-pyridinyl)amino]-1,2-benzisoxazole (1.0 g) and 1-bromo-5-phenylpentane (1.13 g) in acetonitrile (25 mL) was heated under reflux for 24 hr. The mixture was allowed to cool to room temperature, and the precipitate was collected. The precipitate was washed with diethyl ether and dried in vacuo to afford 0.85 g (41%) of product, mp 213°–214° C.

Analysis:

Calculated for C$_{23}$H$_{24}$BrN$_3$O: 63.02% C 5.52% H 9.59% N

Found: 63.02% C 5.47% H 9.62% N

EXAMPLE EIGHT

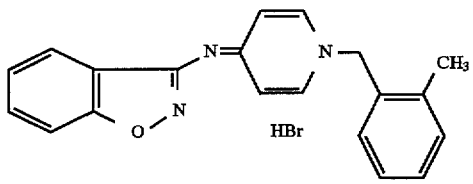

3-[1-(2-Methylphenyl)methyl-N-4(1H)-pyrldiniminyl]-1,2-benzisoxazole hydrobromide.

A mixture of 3-[(4-pyridinyl)amino]-1,2-benzisoxazole (1.0 g) and alpha-bromo-2-xylene (0.63 mL) in acetonitrile (25 mL) was heated under reflux for 24 hr. The mixture was allowed to cool to room temperature, and the precipitate was collected. The precipitate was washed with diethyl ether and dried in vacuo to afford 1.47 g (78%) of product, mp 261°–262° C.

Analysis:

Calculated for C$_{20}$H$_{18}$BrN$_3$O: 60.62% C 4.58% H 10.60% N

Found: 60.35% C 4.45% H 10.63% N

EXAMPLE NINE

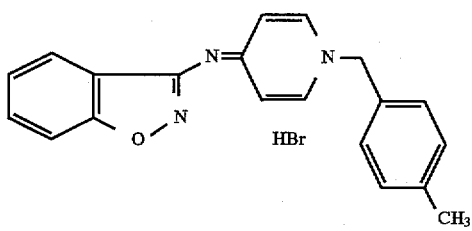

3-[1-(4-Methylphenyl)methyl-N-4(1H)-pyridiniminyl]-1,2-benzisoxazole hydrobromide.

A mixture of 3-[(4-pyridinyl)amino]-1,2-benzisoxazole (1.0 g) and alpha-bromo-4-xylene (0.63 mL) in acetonitrile (25 mL) was heated under reflux for 24 hr. The mixture was allowed to cool to room temperature, and the precipitate was collected. The precipitate was washed with diethyl ether and dried in vacuo to afford 1.43 g (76%) of product, mp 240°–242° C.

Analysis:

Calculated for $C_{20}H_{18}BrN_3O$: 60.62% C 4.58% H 10.60% N

Found: 60.46% C 4.38% H 10.60% N

EXAMPLE TEN

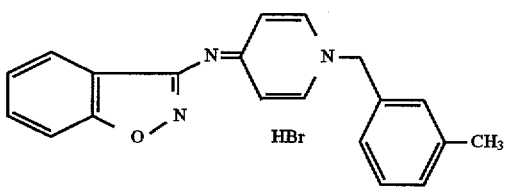

3-[1-(3-Methylphenyl)methyl-N-4(1H)-pyridiniminyl]-1,2-benzisoxazole hydrobromide.

A mixture of 3-[(4-pyridinyl)amino]-1,2-benzisoxazole (1.0 g) and alpha-bromo-3-xylene (0.64 mL) in acetonitrile (25 mL) was heated under reflux for 24 hr. The mixture was allowed to cool to room temperature, and the precipitate was collected. precipitate was washed with diethyl ether and dried in vacuo to afford 1.43 g (76%) of product, mp 232°–233° C.

Analysis:

Calculated for $C_{20}H_{18}BrN_3O$: 60.62% C 4.58% H 10.60% N

Found: 60.70% C 4.63% H 10.41% N

EXAMPLE ELEVEN

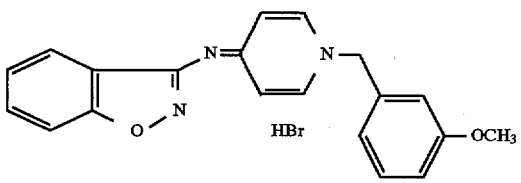

3-[1-(3-Methoxyphenyl)methyl-N-4(1H)-pyridiniminyl]-1,2-benzisoxazole hydrochloride.

A mixture of 3-[(4-pyridinyl)amino]-1,2-benzisoxazole (1.0 g) and 3-methoxybenzyl chloride (0.68 mL) in acetonitrile (25 mL) was heated under reflux for 1 hr. The mixture lo was allowed to cool to room temperature, and the precipitate was collected. The precipitate was washed with diethyl ether and dried in vacuo to afford 0.90 g (52%) of product, mp 244°–245° C.

Analysis

Calculated for $C_{20}H_{18}C_1N_3O_2$: 65.31% C 4.93% H 11.42% N

Found: 65.12% C 4.61% H 11.36% N

EXAMPLE TWELVE

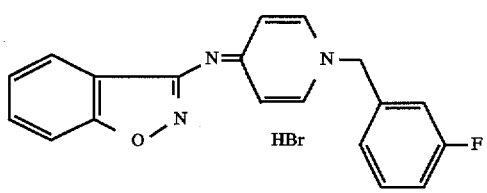

3-[1-(3-Fluorophenyly)methyl-N-4(1H)-pyridiniminyl]-1,2-benzisoxazole hydrobromide A mixture of 3-[(4-pyridinyl)amino]-1,2-benzisoxazole (1.0 g) and 3-fluorobenzyl bromide (0.58 mL) in acetonitrile (25 mL) was heated under reflux for 1 hr. The mixture was allowed to cool to room temperature, and the precipitate was collected. The precipitate was washed with diethyl ether and dried in vacuo to afford 1.40 g (73%) of product, mp 248°–249° C.

Analysis

Calculated for $C_{19}H_{15}BrFN_3O$: 57.02% C 3.78% H 10.50% N

Found: 56.85% C 3.48% H 10.42% N

EXAMPLE THIRTEEN

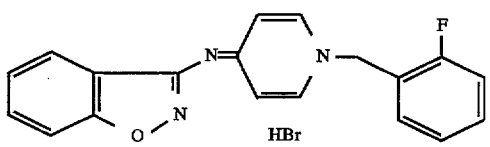

3-[1-(2-Fluorophenyl)methyl-N-4(1H)-pyridiniminyl]1,2-benztsoxazole hydrobromide.

A mixture of 3-[(4-pyridinyl)amino]1,2-benzisoxazole (1.0 g) and 2-fluorobenzyl bromide (0.56 mL) in acetonitrile (25 mL) was heated under reflux for 1 hr. The mixture was allowed to cool to room temperature, and the precipitate was collected. The precipitate was washed with diethyl ether and dried in vacuo to afford 1.43 g (74%) of product, mp 260°–261 ° C.

Analysis

Calculated for $C_{19}H_{15}BrFN_3O$: 57.02% C 3.78% H 10.50% N

Found: 56.77% C 3.87% H 1 10.53% N

EXAMPLE FOURTEEN

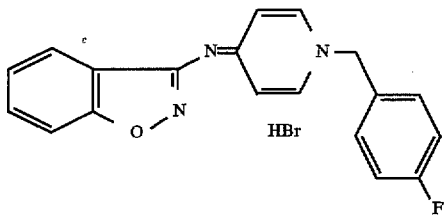

3-[1-(4-Florophenyl)methyl-N-4(1H)-pyridiniminyl]-1,2-benzisoxazole hydrobromide.

A mixture of 3-[(4-pyridinyl)amino]-1,2-benzisoxazole (1.0 g) and 4-fluorobenzyl bromide (0.59 mL) in acetonitrile (25 mL) was heated under reflux for I hr. The mixture was allowed to cool to room temperature, and the precipitate was collected. The precipitate was washed with diethyl ether and dried in vacuo to afford 1.38 g (73%) of product, mp 259°–260° C.

Analysis:

Calculated for $C_{19}H_{15}BrFN_3O$: 57.02% C 8.78% H 10.50% N

Found: 56.79% C 3.85% H 10.54% N

EXAMPLE FIFTEEN

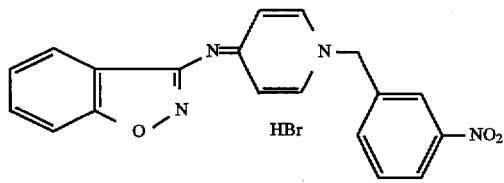

3-[1-(3-Nitrophenyl)methyl-N-4(1H)-pyridiniminyl]-1,2-benzisoxazole hydrochloride.

A mixture of 3-[(4-pyridinyl)amino]-1,2-benzisoxazole (1.0 g) and 3-nitrobenzyl chloride (0.81 g) in acetonitrile (25 mL) was heated under reflux for 24 hr. The mixture was allowed to cool to room temperature, and the precipitate was collected. The precipitate was washed with diethyl ether and dried in vacuo to afford 0.63 g (35%) of product, mp 292°–293° C.

Analysis:

Calculated for $C_{19}H_{15}ClN_4O_3$: 59.62% C 3.95% H 14.64% N

Found: 59.45% C 3.91% H 14.77% N

EXAMPLE SIXTEEN

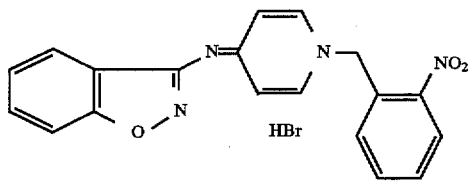

3-[1-(2-Nitrophenyl)methyl-N-4(1H) - pyridiniminyl]-1,2-benzisoxazole hydrobromide.

A mixture of 3-[(4-pyridinyl)amino]-1,2-benzisoxazole (1.0 g) and 2-nitrobenzyl bromide (1.02 g) in acetonitrile (25 mL) was heated under reflux for 1 hr. The mixture was allowed to cool to room temperature, and the precipitate was collected. The precipitate was washed with diethyl ether and dried in vacuo to afford 1.51 g (75%) of product, mp 221°–222° C.

Analysis:

Calculated for $C_{19}H_{15}BrN_4O_3$: 53.41% C 3.54% H 13.11% N

Found: 53.34% C 3.29% H 13.09% N

EXAMPLE SEVENTEEN

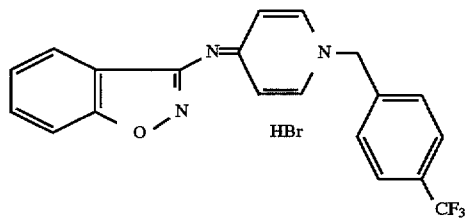

3-[1-(4-Trifluoromethylphenyl)methyl-N-4(1H)-pyridiniminyl]-1,2-benzisoxazole hydrobromide.

A mixture of 3-[(4-pyridinyl)amino]-1,2-benzisoxazole (1.0 g) and 4-trifluoromethylbenzyl bromide (1.13 g) in acetonitrile (25 mL) was heated under reflux for 1 hr. The mixture was allowed to cool to room temperature, and the precipitate was collected. The precipitate was washed with diethyl ether and dried in vacuo to afford 1.67 g (78%) of product, mp 245°°–246° C.

Analysis

Calculated for $C_{20}H_{15}BrF_3N_3O$: 53.35% C 3.36% H 9.33% N

Found: 53.17% C 3.39% H 9.24% N

EXAMPLE EIGHTEEN

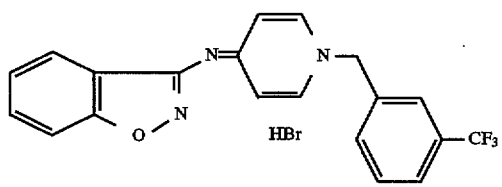

3-[1-(3-Trifluoromethylphenyl)methyl-N-4(1H)-pyridiniminyl]-1,2-benztsoxazole hydrochloride.

A mixture of 3-[(4-pyridinyl)amino]-1,2-benzisoxazole (1.0 g) and 3-trifluoromethylbenzyl chloride (0.73 mL) in acetonitrile (25 mL) was heated under reflux for 1 hr. The mixture was allowed to cool to room temperature, and the precipitate was collected. The precipitate was washed with diethyl ether and dried in vacuo to afford 0.52 g (27%) of product, mp 254°–255° C.

Analysis

Calculated for $C_{20}H_{15}ClF_3N_3O$: 59.20% C 3.73% H 10.35% N

Found: 59.02% C 3.64% H 10.35% N

EXAMPLE NINETEEN

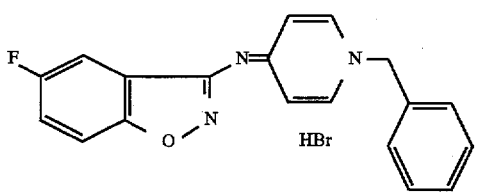

5-Fluoro-3-[1-phenylmethyl-N-4(1H)-pyridiniminyl]-1,2-benzisoxazole hydrobromide.

A mixture of 5-Fluoro-3-[4-pyridinyl-amino]-1,2-benzisoxazole (0.70 g) and benzyl bromide (0.52 g) in acetonitrile (15 mL) was heated under reflux for 1.5 hr. The mixture was allowed to cool to room temperature, and the precipitate was collected. The precipitate was washed with diethyl ether and dried in vacuo to afford 1.16 g (95%) of product, mp 276°–277° C.

Analysis

Calculated for $C_{19} H_{15}$ Br $FN_3O$: 57.02% C 3.78% H 10.50% N

Found: 57.04% C 3.74% H 10.42% N

EXAMPLE TWENTY

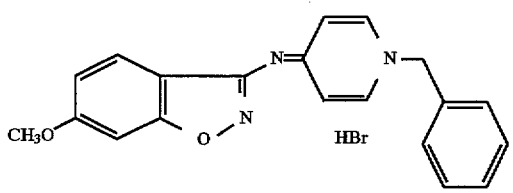

6-Methoxy-3-[1-phenylmethyl-N-4(1H)-pyridiniminyl]-1,2-benzisoxazole hydrobromide.

A mixture of 6-methoxy-3-[4-pyridinyl)amino]-1,2-benzisoxazole (0.85 g) and benzyl bromide (0.60 g) in acetonitrile (18 mL) was heated under reflux for 1.5 hr. The mixture was allowed to cool to room temperature, and the precipitate was collected. The precipitate was washed with diethyl ether and dried in vacuo to afford 1.26 g (87%) of product, mp 264°–265° C.

Analysis

Calculated for $C_{20}H_{18}BrN_3O_2$: 58.26% C 4.40% H 10.19% N

Found: 57.89% C 4.44% H 10.11% N

EXAMPLE TWENTY-ONE

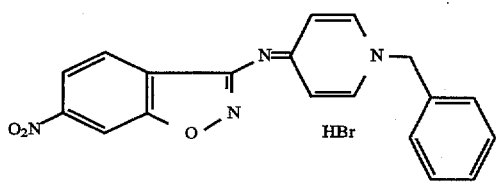

6-Nitro-3-[1-phenylmethyl-N-4(1H)-pyridiniminyl]-1,2-benzisoxazole hydrobromide.

A mixture of 6-nitro-3-[(4-pyridinyl)amino]-1,2-benzisoxazole (0.80 g) and benzyl bromide (0.53 g) in acetonitrile (15 mL) was heated under reflux for 1.5 hr. The mixture was allowed to cool to room temperature, and the precipitate was collected. The precipitate was washed with diethyl ether and dried in vacuo to afford 1.23 g (92%) of product mp 270°–272° C.

Analysis:

Calculated for $C_{19}H_{15}BrN_4O_3$: 53.41% C 3.54% H 13.11% N

Found: 58.:31% C 3.32% 3.32% H 13.12% N

EXAMPLE TWENTY-TWO

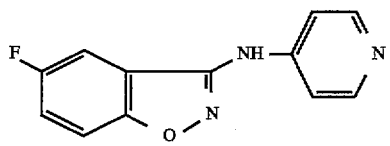

5-Fluoro-3-[4-(pyridinyl)amino]-1,2-benzisoxazole.

A mixture of 2,5-difluoro-N-4-pyridinylbenzamide (10 g) and thionyl chloride (45 mL) was heated under reflux for 3 hr. The reaction mixture was evaporated in vacuo, and the residual imidoyl chloride was used without purification. O-Trimethylsilylhydroxyl amine (10.3 g) was added rapidly to a suspension of the imidoyl chloride in tetrahydrofuran (215 mL), and the mixture was stirred at room temperature for 18 hr. The reaction mixture was filtered, the solids were treated with saturated sodium bicarbonate solution, and the mixture was extracted with ethyl acetate. The tiltrate was treated dropwise with tetra-n-butylammonium fluoride solution (1M in tetrahydrofuran, 42.7 mL). The solution was stirred at room temperature for 10 min., diluted with water and extracted with ethyl acetate. The combined organic extracts were washed with water and saturated sodium chloride solution, dried over anhydrous magnesium sulfate, filtered, and the flitrate was concentrated. The residue was washed with methanol. The tiltrate was combined with the aqueous phase and basified with saturated sodium bicarbonate solution. The layers were separated, and the aqueous phase was extracted with ethyl acetate. The combined organic extracts were washed with water and saturated sodium chloride solution, dried over anhydrous magnesium sulfate, filtered, and the tiltrate was concentrated. The residue was washed with ethyl acetate to give amidoxime; the total amount of amidoxime was 6.2 g (58%), used below without further purification.

Potassium-t-butoxide (1.97 g) was added to a portion of the amidoxime (4.0 g ) suspended in tetrahydrofuran (80 mL), and the mixture was heated under reflux for 12 hr. The reaction mixture was allowed to cool to room temperature and was diluted with water and ethyl acetate. The layers were separated and the aqueous layer was extracted with ethyl acetate. The combined organic extracts were washed with water and saturated sodium chloride solution, dried over anhydrous magnesium sulfate, filtered, and the tiltrate was concentrated. Recrystallization of the residue from acetonitrile provided 2.55 g (69%) of product, mp 248°–249° C.

Analysis

Calculated for $C_{12}H_8FN_3O$: 62.88% C 3.52% H 18.33% N

Found: 62.74% C 3.51% H 18.35% N

EXAMPLE TWENTY-THREE

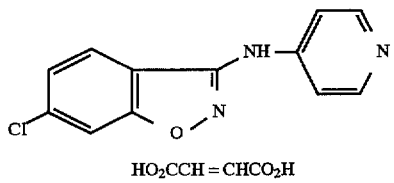

HO₂CCH=CHCO₂H

6-Chloro-3[(4-pyridyl)amino]-1,2-benzisoxazole maleate.

To a solution of 3-amino-6-chloro-1,2-benzisoxazole (5.0 g) in N-methylpyrrolidone (60 mL) was added 4-chloropyridine hydrochloride (9.1 g). The mixture was stirred vigorously at 130° C. for 1.5 hr. The reaction mixture was cooled, saturated sodium bicarbonate solution and water were added. The precipitate was collected, washed with water, air dried, and flash chromatographed on silica (7×15 cm column), eluting first with ethyl acetate and then with 10% methanol/ethyl acetate. The appropriate fractions were collected and concentrated. The maleate was formed by treatment of the residue with maleic acid in methanol. Recrystallization from ethanol gave 1.17 g (10.9%) of product, mp 203(dec), after drying under high vacuum and refluxing xylenes.

Analysis

Calculated for $C_{16}H_{12}ClN_3O_5$: 53.13% C 3.34% H 11.62% N

Found: 53.02% C 3.14% H 11.44% N

EXAMPLE TWENTY-FOUR

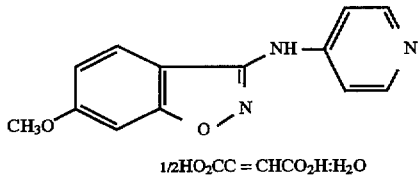

1/2HO₂CC=CHCO₂H:H₂O

6-Methoxy-3-[4-(pyridinyl)amino]1,2-benzisoxazole hemi-fumarate monohydrate

A mixture of 2-fluoro-4-methoxy-N-4-pyridinylbenzamide (11.0 g) and thionyl chloride (16 g) in dichloroethane (10 mL) was heated under reflux for 1 hr, and the reaction mixture was allowed to cool to room temperature. Diethyl ether was added, and the imidoyl chloride was collected by filtration.

O-Trimethylsilylhydroxyl amine (10.6 g) was added rapidly to a suspension of the imidoyl chloride in tetrahydrofuran (220 mL), and the resulting mixture was stirred at room temperature for 20 hr. The reaction mixture was diluted with ethyl acetate and basified with saturated sodium bicarbonate solution. The layers were separated and the aqueous phase was extracted with ethyl acetate. The combined organic extracts were washed with water and saturated sodium chloride solution, dried over anhydrous magnesium sulfate, filtered, and the flitrate was concentrated. Trituration of the residue with ethyl acetate provided 9.3 g of amidoxime, used below without further purification.

Potassium-t-butoxide (0.54 g) was added to a portion of the amidoxime (1.2 g) in dimethylformamide (23 mL), and the mixture was heated at 60° C. for 1 hr. The reaction mixture was allowed to cool to room temperature and diluted with saturated ammonium chloride solution and ethyl acetate. The layers were separated and the aqueous layer was extracted with ethyl acetate. The combined organic extracts were washed with water and saturated sodium chloride solution, dried over anhydrous magnesium sulfate, filtered, and the tiltrate was concentrated. The residue was chromatographed on a RAPTLC (Chromatotron®, 4 mm plate), eluting with methanol/ethyl acetate. The appropriate fractions were collected and concentrated to provide 0.55 g (50%) of product free base. The product free base was dissolved in hot methanol and treated with an equivalent amount of fumaric acid. The precipitate was collected to afford 0.51 g of analytically pure product, mp 261°–263° C.

Analysis

Calculated for $C_{13}H_{13}N_3O_3 \cdot 0.5C_4H_4$: 56.78% C 4.77% H 13.24% N

Found: 56.65% C 4.74% H 12.98% N

EXAMPLE TWENTY-FIVE

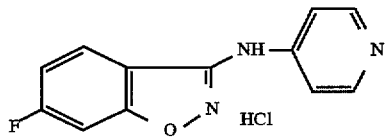

6-Fluoro-3-[4-pyridinyl)amino]-1,2-benzisoxazole hydrochloride.

A mixture of 2,4-difluoro-N-4-pyridinylbenzamide (10 g) and thionyl chloride (15 g) was heated under reflux for 1 hr, and the reaction mixture was allowed to cool to room temperature. Diethyl ether was added, and the imidoyl chloride was collected. O-Trimethylsilylhydroxyl amine (10.3 g) was added rapidly to a suspension of the imidoyl chloride formed above in tetrahydrofuran (210 mL), and the mixture was stirred at room temperature for 18 hr. The reaction mixture was diluted with ethyl acetate and basified with saturated sodium bicarbonate solution. The layers were separated and the aqueous layer was extracted with ethyl acetate. The combined organic extracts were washed with water and saturated sodium chloride solution, dried over anhydrous magnesium sulfate, filtered, and the tiltrate was concentrated. Trituration of the residue with ethyl acetate provided 5.74 g) of amidoxime, used below without further purification.

Potassium-t-butoxide (2.3 g) was added to a portion of the amidoxime (4.7 g) suspended in tetrahydrofuran (100 mL), and the mixture was heated under reflux for 0.75 hr. The reaction mixture was allowed to cool to room temperature and was diluted with water and ethyl acetate. The layers were separated and the aqueous layer was extracted with ethyl acetate. The combined organic extracts were washed with water and saturated sodium chloride solution, dried over anhydrous magnesium sulfate, filtered, and the tiltrate was concentrated. Recrystallization of the residue from ethyl acetate/methanol provided 2.47 g (54%) of product free base in two crops. The flitrates were concentrated, and the residue was recrystallized. Recrystallization of the residue left after concentration of the mother liquors from acetonitrile provided an additional 1.12 g (26%) of product free base. A portion of the product free base (1 g) was dissolved in hot methanol and treated with methanolic hydrochloric acid. The precipitate was collected by filtration to afford 0.67 g of analytically pure product, mp>300° C.

Analysis

Calculated for C₁₂H₉ClFN₃O: 54.25% C 3.41% H 15.82% N

Found: 54.07% C 3.64% H 15.80% N

EXAMPLE TWENTY-SIX

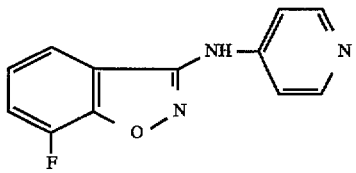

7-Fluoro-3-(4-pyridinylamino)-1,2-benzisoxazole.

A mixture of 2,3-difluoro-N-4-pyridinylbenzamide (10 g) in thionyl chloride (45 mL) was heated under reflux for 4 hr., the reaction mixture was allowed to cool to room temperature and concentrated in vacuo. Dichloroethane and diethyl ether were added. The precipitated imidoyl chloride (10.0 g) was collected. O-Trimethylsilylhydroxyl amine (10.3 g) was added rapidly to a suspension of the imidoyl chloride formed above in tetrahydrofuran (210 mL), and the mixture was stirred at room temperature for 18 hr. 10% Hydrochloric acid (50 mL) was added, and the reaction mixture was stirred at room temperature for 1 hr. The solution was basified with saturated sodium bicarbonate solution and extracted with ethyl acetate. The layers were separated and the aqueous layer was extracted with ethyl acetate. The combined organic extracts were washed with water and saturated sodium chloride solution, dried over anhydrous magnesium sulfate, filtered, and the tiltrate was concentrated. Trituration of the residue with ethyl acetate provided 5.9 g of amidoxime, used below without further purification.

Potassium-t-butoxide (1.1 g) was added to a portion of the amidoxime (2.25 g) suspended in tetrahydrofuran (45 mL), and the mixture was heated under reflux for 4 hr. The reaction mixture was allowed to cool to room temperature and diluted with water and ethyl acetate. The layers were separated and the aqueous layer was extracted with ethyl acetate. The combined organic extracts were washed with water and saturated sodium chloride solution, dried over anhydrous magnesium sulfate, filtered, and the tiltrate was concentrated. Recrystallization of the residue from acetonitrile provided 1.25 g (61%) of product, mp 234°–236° C.

Analysis

Calculated for C₁₂H₉FN₃O: 62.88% C 8.52% H 18.88% N

Found: 62.63% C 3.35% H 18.47% N

EXAMPLE TWENTY-SEVEN

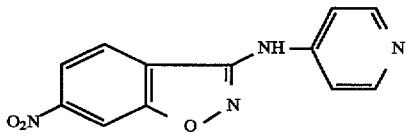

6-Nitro-3-(4-pyridinylamino)-1,2-benzisoxazole.

A mixture of 2,4-dinitro-N-4-pyridinylbenzamide (14.4 g) and phosphorus pentachloride (12.5 g) in dichloroethane (100 mL) was heated under reflux for 4 hr. The reaction mixture was allowed to cool to room temperature and the precipitated imidoyl chloride (13.2 g) was collected. O-Trimethylsilylhydroxyl amine (12.1 g) was added rapidly to a suspension of the imidoyl chloride in tetrahydrofuran (200 mL), and the mixture was stirred at room temperature for 18 hr. Subsequent addition of water precipitated a solid (4.06 g) which was collected by filtration. The fillrate was basified with saturated sodium bicarbonate solution and extracted with ethyl acetate. The layers were separated and the aqueous layer was extracted with ethyl acetate. The combined organic extracts were washed with water and brine, dried over anhydrous magnesium sulfate, filtered, and the tiltrate was concentrated. Trituration of the residue with ethyl acetate and then hot methanol gave 1.81 g of product. Combination of the two batches provided 5.86 g (39%) of amidoxime, which was used below without further purification.

Potassium-t-butoxide (2.1 g) was added to a portion of the amidoxime (5.3 g) suspended in tetrahydrofuran (80 mL), and the mixture was heated under reflux for 2 hr. The reaction mixture was allowed to cool to room temperature and diluted with water and ethyl acetate. The layers were separated and the aqueous phase was extracted with ethyl acetate. The combined organic extracts were washed with water and brine, dried over anhydrous magnesium sulfate, filtered, and the tiltrate was concentrated. Recrystallization of the residue from acetonitrile provided 3.32 g (74%) of product, mp 296°–300 ° C.

Analysis

Calculated for C₁₂H₈N₄O₃: 62.88% C 3.52% H 18.33% N

Found: 62.63% C 3.35% H 18.47% N

EXAMPLE TWENTY-EIGHT

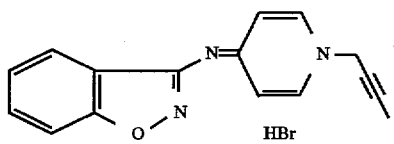

3-[1-(2-butynyl)-N-4(1H)-pyridiniminyl]-1,2-benzisoxazole hydrobromide.

A mixture of 3-(4-pyridinylamino)-1,2-benzisoxazole (0.9 g) and 4-bromo-2-butyne (0.86 g) in acetonitrile (25 mL) was heated under reflux for 1 hr. The reaction mixture was allowed to cool to room temperature and the precipitate was collected. The precipitate was washed with diethyl ether and recrystallized from ethanol to afford product, mp 229°–230° C.

Analysis

Calculated for C₁₆H₁₄BrN₃O: 55.83% C 4.10% H 12.21% N

Found: 55.54% C 3.99% H 12.36% N

EXAMPLE TWENTY-NINE

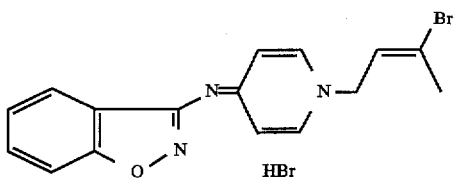

3-[1-(3-bromo-2-butenyl)-N-4(1H)-pyridiniminyl]-1, 2-benzisoxazole hydrobromide.

A mixture of 3-(4-pyridinylamino)-1,2-benzisoxazole (1 g) and 2,4-dibromo-2-butene (1.51 g) in acetonitrile (25 mL) was heated under reflux for 1 hr. The reaction mixture was allowed to cool to room temperature, and the precipitate was collected. The precipitate was washed with diethyl ether and dried in vacuo to afford 1.3 g (65%) of product, mp 217°–218° C.

Analysis

Calculated for $C_{16}H_{15}Br_2N_3O$: 45.20% C 8.56% H 9.88% N

Found: 45.36% C 3.74% H 9.94% N

EXAMPLE THIRTY

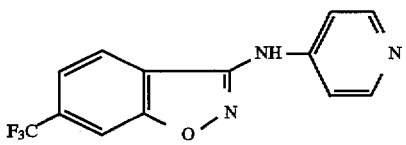

6-Trifluoromethyl-3-(4-pyridinylamino)-1,2-benzisoxazole.

A mixture of 2-fluoro-4-trifluoromethyl-N-4-pyridinylbenzamide (29 g, 101.8 mmol) and phosphorous pentachloride (15.9 g, 1.2 eq) in dichloroethane (750 mL) was heated at reflux for one hour. The reaction mixture was allowed to cool to room temperature and diethyl ether was subsequently added. The precipitated imidoyl chloride (25 g) was collected by filtration. 0-Trimethylsilylhydroxyl amine (19.0 g, 2.2 eq) was added rapidly to a suspension of the imidoyl chloride formed above in tetrahydrofuran (750 mL), and the resulting mixture was stirred at room temperature for 20 hours. Dilute hydrochloric acid was added, and the mixture was stirred 10 minutes at room temperature. The reaction was diluted with ethyl acetate and carefully basified with saturated sodium bicarbonate solution. The layers were separated and the organic phase was dried over anhydrous magnesium sulhte, filtered and concentrated under vacuum. The crude product (14.7 g) was triturated with ethyl acetate to provide the amidoxime (12.7 g). The amidoxime was dissolved in THF and potassium butoxide (5.2 g, 1.1 eq) was added in one portion. The reaction was stirred at room temperature for 2 hours. The reaction was diluted with water and ethyl acetate. The organic layer was collected and washed with water and brine, dried over anhydrous magnesium sulfate, filtered and concentrated under vacuum. The residue was triturated with ethyl acetate to provide the title compound (7.5 g, 63%). The title compound is recrystallized from methanol, mp 249°–250° C.

Analysis

Calculated for $C_{13}H_8F_3N_3O$: 55.92% C 2.89% H 15.05% N

Found: 55.76% C 2.73% H 15.13% N

EXAMPLE THIRTY-ONE

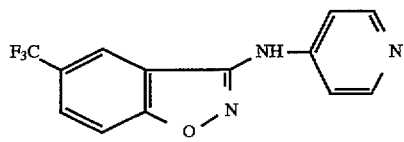

5-Trifluoromethyl-3-(4-pyridinylamino)-1,2-benzisoxazole.

Synanti 2-fluoro-5-trifluoromethylphenyl-4-pyridinylamino methanone oxime (10.7 g, 35.8 mmol) was dissolved in THF (400 mL) and potassium butoxide (4.4 g, 1.1 eq) was added in one portion. The reaction was stirred for 6 hours at room temperature under nitrogen. The reaction was diluted with water and ethyl acetate. The organic layer was collected and washed with water and brine, dried over anhydrous magnesium sulfate, filtered and concentrated under vacuum. Trituration with ethyl acetate provided the title compound (7.0 g, 70%). The title compound is recrystallized from methanol, mp >280° C.

Analysis

Calculated for $C_{13}H_8F_3N_3O$: 55.92% C 2.89% H 15.05% N

Found: 55.88% C 2.69% H 15.01% N

EXAMPLE THIRTY-TWO

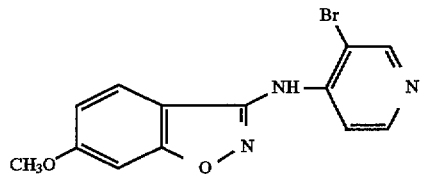

6-Methoxy-3-[4-(3-bromopyridinyl)amino]-1,2-benzisoxazole.

N-Bromosuccinimide (1.8 g, 1.1 eq) was added in one portion to a slurry of 6-methoxy-3-[4-pyridinylamino]-1,2-benzisoxazole (2.2 g, 9.1 mmol) and silica gel 60 (3.0 g) in carbon tetrachloride (50 mL). The mixture was refluxed for one hour and subsequently stirred overnight at room temperature. The reaction was filtered and the tiltrate was washed with aqueous sodium thiosulfate, dried over anhydrous sodium sulfate, filtered and concentrated under vacuum. The residue was purified on a Prep 500 Chromatograph (silica gel, 2% methanol/ethyl acetate) to provide the title compound (0.97 g, 33%). The title compound is recrystallized from methanol, mp 152°–153° C.

Analysis

Calculated for $C_{13}H_{10}BrN_3O_2$: 48.77% C 3.15% H 13.13% N

Found: 48.60% C 8.2,1% H 18.13% N

EXAMPLE THIRTY-THREE

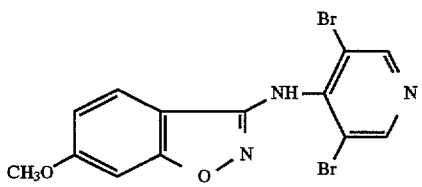

6-Methoxy-3-[4-(3,5-dibromopyridinyl)amino]-1,2-benzisoxazole.

In a manner analogous to the procedure described in example thirty-two, the title compound (0.95 g, 26%) is prepared from 6-methoxy-3-[4-pyridinylamino]-1,2-benzisoxazole (2.2 g, 9.1 mmol). The title compound is recrystallized from methanol, mp 180°–181° C.

EXAMPLE THIRTY-FOUR

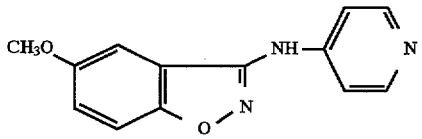

5-Methoxy-3-(4-pyridinylamino)-1,2-benzisoxazole.

In a manner analogous to the procedure described in example twenty-five, the title compound (1.2 g, 20% after recrystallization from acetonitrile, mp 248°–251 ° C.) is prepared from 2-fluoro-5-methoxy-N-4-pyridinylbenzamide (9.39 g, 38.2 mmol). In the last step, the intermediate is heated in N-methyl pyrrolidinone at approximately 100° C. to provide the title compound.

EXAMPLE THIRTY-FIVE

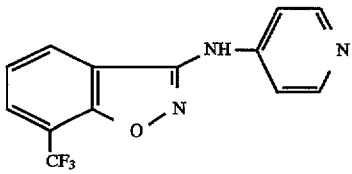

3-(4-Pyridinylamino)-7-trifluoromethyl-1,2-benzisoxazole.

In a manner analogous to the procedure described in example thirty, the title compound (4.35 g, 76%, after recrystallization from acetonitrile, 248°–249° C. (dec)) is prepared from 2-fluoro-N-(4-pyridinyl)-3-trifluoromethyl benzamide (10 g, 35.2 mmol).

EXAMPLE THIRTY-SIX

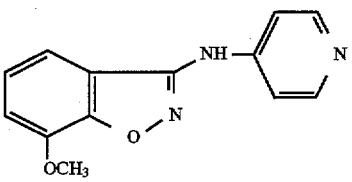

7-Methoxy-3-(4-pyridinylamino)-1,2-benzisoxazole.

In a manner analogous to the procedure described in example thirty, the title compound (3.0 g, 65%, after recrystallization from acetonitrile, 226°–227° C.) is prepared from 2-fluoro-3-methoxy-N-4-pyridinylbenzamide (25 g, 102 mmol). In the last step, the intermediate is heated in N-methyl-pyrrolidinone at approximately 100° C. to provide the title compound.

EXAMPLE THIRTY-SEVEN

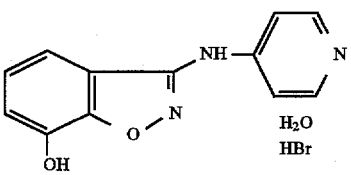

3-(4-pyridinylamino)-1,2-benzisoxazole-7-ol hydrobromide monohydrate.

A solution of 7-methoxy-3-[(4-pyridinyl)amino]1,2-benzisoxazole (3 g, 12.4 mmol) in 124 mL of a 1:1 mixture of 48% Hbr and acetic acid was heated at reflux for 24 hours. Subsequently, the mixture was allowed to cool to room temperature, and the precipitated product was collected by filtration. The white solid was washed with diethyl ether and dried under vacuum to provide the title compound (3.1 g, 78%), mp 270°–273° C.

Analysis:

Calculated for $C_{12}$ $H_{12}BrN_3O_3$: 44.19% C 3.71% H 12.88% N

Found: 43.79% C 3.79% H 12.84% N

EXAMPLE THIRTY-EIGHT

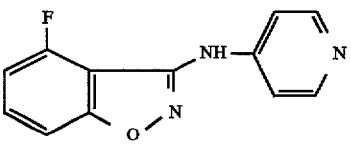

4-fluoro-3-(4-pyridinylamino)-1,2-benzisoxazole.

In a manner analogous to the procedure described in example twenty-five, the title compound (2.1 g, 43%) is prepared from 2,6-difluoro-N-4-pyridinylbenzamide (5 g, 21.4 retool). The title compound is recrystallized from hot ethyl acetate, mp 160°–161° C.

Analysis

Calculated for $C_{12}H_8FN_3O$: 62.88% C 3.52% H 18.3% N

Found: 62.72% C 3.71% H 18.21% N

EXAMPLE THIRTY-NINE

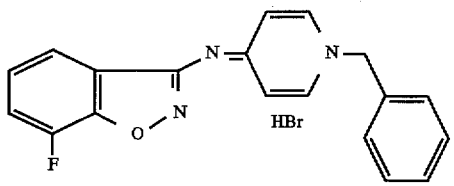

7-Fluoro-3-[1-phenylmethyl-N-4(1H)-pyridiniminyl]-1,2-benzisoxazole hydrobromide.

A mixture of 7-fluoro-3-[(4-pyridinyl)amino]-1,2-benzisoxazole (0.70 g, 3.05 mmol) and benzyl bromide (0.52 g, 3.05 mmol) in acetonitrile (15 mL) was heated at reflux for 1.5 hours. Subsequently, the mixture was allowed to cool to room temperature and the precipitated product was collected by filtration. The white solid was washed with diethyl ether and dried under vacuum to provide the title compound (1.16 g, 95%), mp >300° C.

Analysis:

Calculated for $C_{19}H_{15}BrFN_3O$: 57.02% C 3.78% H 10.50% N

Found: 56.78% C 8.67% H 10.73% N

EXAMPLE FORTY

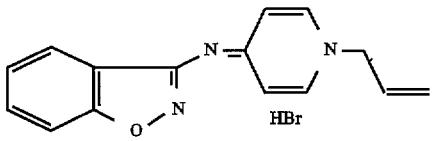

3-[1-(2-propenyl)-N-4(1H)-pyridiniminyl]-1,2-benzisoxazole hydrobromide.

A mixture of 3-[(4-pyridinyl)amino]-1,2-benzisoxazole (1.0 g, 4.73 mmol) and allyl bromide (0.45 mL, 1 eq) in acetonitrile (25 mL) was heated at reflux for one hour. The mixture was then allowed to cool to room temperature and the precipitated product was collected by filtration. The white solid was washed with diethyl ether and dried under vacuum to provide the title compound (1.15 g, 73%), mp 250°–251° C.

Analysis

Calculated for $C_{15}H_{14}BrN_3O$: 54.23% C 4.25% H 12.65% N

Found: 54.05% C 4.21% H 12.58% N

EXAMPLE FORTY-ONE

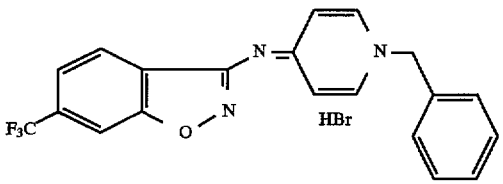

3-[1-(phenylmethyl)-N-4(1H)-pyridiniminyl]-6-trifluoromethyl-1,2-benzisoxazole hydrobromide.

A mixture of 6-trifluoromethyl-3-(4-pyridinylamino)-1,2-benzisoxazole (1 g, 3.58 mmol) and benzyl bromide (0.51 mL, 1.2 eq) in acetonitrile (25 mL) was heated to reflux for one hour. The mixture was then allowed to cool to room temperature and the precipitated product was collected by filtration. The white solid was washed with diethyl ether and dried under vacuum to provide the title compound (1.2 g, 74%), mp 244–245° C.

Analysis

Calculated for $C_{20}H_{15}BrF_3N_3O$: 53.35% C 3.36% H 9.33% N

Found: 53.23% C 3.28% H 9.22% N

EXAMPLE FORTY-TWO

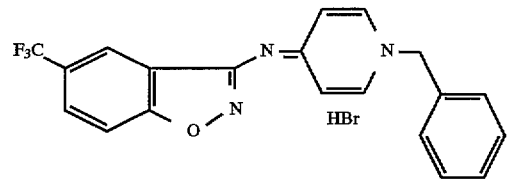

3-[1-(phenylmethyl)-N-4(1H)-pyridiniminyl]-5-trifluoromethyl-1,2-benzisoxazole hydrobromide.

A mixture of 5-trifluoromethyl-3-(4-pyridinylamino)-1,2-benzisoxazole (1 g, 3.58 mmol) and benzyl bromide (0.51 mL, 1.2 eq) in acetonitrile (25 mL) was heated to reflux for one hour. The mixture was then allowed to cool to room temperature and the precipitated product was collected by filtration. The white solid was washed with diethyl ether and dried under vacuum to provide the title compound (1.3 g, 81%), mp 274°–275° C.

Analysis

Calculated for $C_{20}H_{15}BrF_3N_3O$: 53.35% C 3.36% H 9.33% N

Found: 53.16% C 3.34% H 9.38% N

EXAMPLE FORTY-THREE

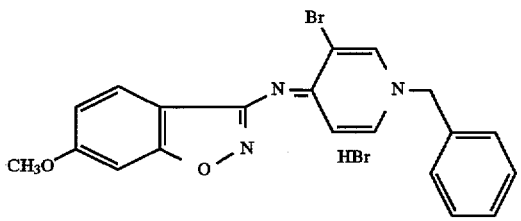

6-Methoxy-3-[1-phenylmethyl-N-4(1H)-3-bromo-pyridiniminyl]-1,2-benzisoxazole hydrobromide.

A mixture of 6-methoxy-3-[4-(3-bromopyridinyl)amino]-1,2-benzisoxazole (0.7 g, 2.2 mmol) and benzyl bromide (0.31 mL, 1.2 eq) in acetonitrile (25 mL) was heated to reflux for one hour. The mixture was then allowed to cool to room temperature and the precipitated product was collected by filtration. The white solid was washed with diethyl ether and dried under vacuum to provide the title compound (0.48 g, 45%), mp 241°–242° C.

Analysis

Calculated for $C_{20}H_{17}Br_2N_3O_2$: 48.91%13 3.49% H 8.55% N

Found: 48.75%t3 3.48% H 8.52% N

EXAMPLE FORTY-FOUR

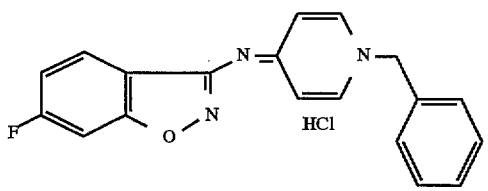

6-Fluoro-3-[1-phenylmethyl-N-4(1H)-pyridiniminyl]-1,2-benzisoxazole hydrochloride.

A mixture of 6-fluoro-3-[(4-pyridinyl)amino-1,2-benzisoxazole (0.70 g, 3.05 mmol) and benzyl bromide (0.52 g, 3.05 mmol) in acetonitrile (15 mL) was heated at reflux for 1.5 hours. The mixture was allowed to cool to room temperature and the precipitated product was collected by filtration. The white solid was washed with diethyl ether and dried under vacuum to provide a white powder (1.1 g). The white powder was treated with saturated sodium bicarbonate to make basic and the aqueous solution was extracted with ethyl acetate. The combined organic extracts were concentrated under vacuum to provide the free base of the title compound (0.65 g). The free base was dissolved in hot isopropanol and treated with a solution of HCl (g) in isopropanol. After cooling, the title compound was collected by filtration (0.39 g, 36%), mp 267°–269° C (dec).

Analysis:

Calculated for $C_{19}H_{15}ClFN_3O$: 64.14% C 4.25% H 11.81% N

Found: 63.79% C 4.31% H 11.47% N

EXAMPLE FORTY-FIVE

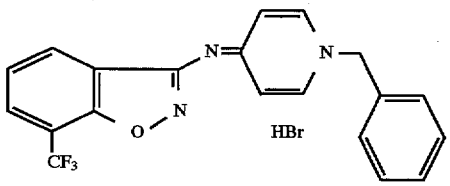

3-[1-Phenylmethyl-N-4(1H)ypyridiniminyl]-7-trifluoromethyl-1,2-benzisoxazole hydrobromide.

A mixture of 3-[(4-pyridinyl)amino]-7-trifluoromethyl-1,2-benzisoxazole (0.80 g, 2.87 mmol) and benzyl bromide (0.49 g, 2.87 mmol) in acetonitrile (15 mL) was heated at reflux for 1.5 hours. The mixture was allowed to cool to room temperature and the precipitated product was collected by filtration. The white solid was washed with diethyl ether and dried under vacuum to provide the title corapound (0.99 g, 77%), rap 275°–277° C (dec).

Analysis:

Calculated for $C_{20}H_{15}BrF_3N_3O$: 53.35% C 8.36% H 9.88% N

Found: 53.14% C 3.33% H 9.55% N

EXAMPLE FORTY-SIX

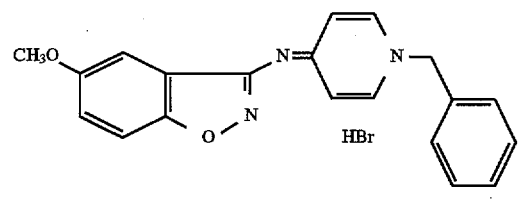

5-Methoxy-3-[1-phenylmethyl-N-4(1H)-pyridiniminyl]-1,2-benzisoxazole hydrobromide.

A mixture of 5-methoxy-3-[(4-pyridinyl)amino]-1,2-benzisoxazole (0.70 g, 2.9 mmol) and benzyl bromide (0.5 g, 2.9 retool) in acetonitrile (15 mL) was heated at reflux for 1.5 hours. The mixture was allowed to cool to room temperature and the precipitated product was collected by filtration. The white solid was washed with diethyl ether and dried under vacuum to provide the title compound (1.09 g, 91%), mp 277°–278° C (dec).

Analysis

Calculated for $C_{20}H_{18}BrN_3O_2$: 58.26% C 4.40% H 10.19% N

Found: 58.11% C 4.30% H 10.32% N

EXAMPLE FORTY-SEVEN

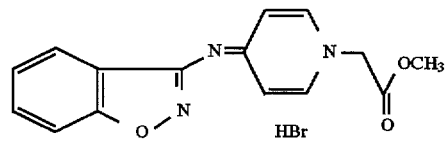

[4-(3-Benzo[d]isoxazolylimino)-1-(4H)-pyridinyl]-acetic acid methyl ester hydrobromide.

A mixture of 3-(4-pyridinylamino)-1,2-benzisoxazole (0.9g, 4.3 mmol) and methyl bromoacetate (0.44 mL, 1.1 eq) in acetonitrile (25 mL) was heated at reflux for one hour. The mixture was then allowed to cool to room temperature and the precipitated product was collected by filtration. The white solid was washed with diethyl ether and dried under vacuum to provide the title compound (1.1 g, 70%), mp 235°–236° C.

Analysis

Calculated for $C_{15}H_{14}BrN_3O_3$: 49.47% C 3.87% H 11.54% N

Found: 49.48% C 3.90% H 11.67% N

EXAMPLE FORTY-EIGHT

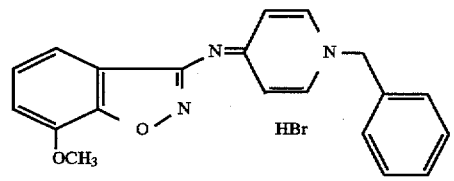

7-Methoxy-3-[1-phenylmethyl-N-4(1H)-pyridiniminyl]-1,2-benzisoxazole hydrobromide.

A mixture of 7-methoxy-3-[(4-pyridinyl)amino]-1,2-benzisoxazole (0.70 g, 2.9 mmol) and benzyl bromide (0.5 g, 2.9 retool) in acetonitrile (15 mL) was heated at reflux for 1.5 hours. The mixture was then allowed to cool to room temperature and the precipitated product was collected by filtration. The white solid was washed with diethyl ether and dried under vacuum to provide the title compound (0.99 g, 83%), mp 253°–254° C (dec).

Analysis

Calculated for $C_{20}H_{18}BrN_3O_2$: 58.26% C 4.40% H 10.19% N

Found: 57.99% C 4.56% H 10.26% N

EXAMPLE FORTY-NINE

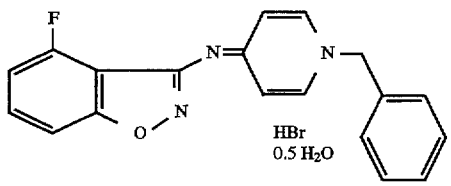

4-Fluoro-3-[1-phenylmethyl-N-4(1H)-pyridiniminyl]-1,2-benzisoxazole hydrobromide hemihydrate.

A mixture of 4-fluoro-3-[(4-pyridinyl)amino]-1,2-benzisoxazole (0.8 g, 3.5 mmol and benzyl bromide (0.42 g, 1 eq) in acetonitrile (50 mL) was heated at reflux for one hour. The mixture was then allowed to cool to room temperature and the precipitated product was collected by filtration. The white solid was washed with diethyl ether to provide the title compound (0.8g, 57%). The title compound is recrystallized from methanol/isopropanol, mp 200°–20 ° C.

Analysis

Calculated for $C_{19}H_{15}BrFN_3O·0.5H_2O$: 55.75% C 3.95% H 10.27% N

Found: 56.11% C 4.03% H 10.51% N

EXAMPLE FIFTY

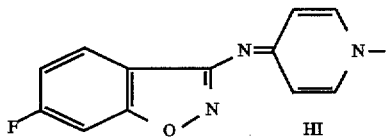

6-Fluoro-3-[1-methyl-N-4(1H)-pyridiniminyl]-1,2-benzisoxazole hydroiodide.

A mixture of 6-fluoro-3-[(4-pyridinyl)amino]-1,2-benzisoxazole (1.43 g, 6.24 mmol) and methyl iodide (0.89 g, 6.24 mmol) in acetonitrile (30 mL) was heated at reflux for 1.5 hours. The mixture was then allowed to cool to room temperature and the precipitated product was collected by filtration. The slightly yellow solid was washed with diethyl ether and dried under vacuum to provide the title compound (193 g, 83%), mp 272°–275° C (dec).

Analysis

Calculated for $C_{13}H_{11}FIN_3O$: 42.07%(3 2.99% H 11.82% N

Found: 42.07%G 2.92% H 11.31% N

EXAMPLE FIFTY-ONE

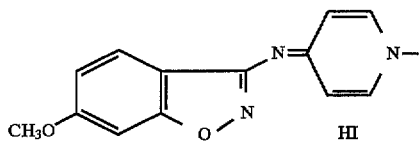

6-Methoxy-3-[1-methyl-N-4(1H)-pyridiniminyl]-1,2-benzisoxazole hydroiodide.

A mixture of 6-methoxy-3-[(4-pyridinyl)amino]-1,2-benzisoxazole (1.1 g, 4.56 mmol) and methyl iodide (0.65 g, 4.56 mmol) in acetonitrile (20 mL) was heated at reflux for 1.5 hours. The mixture was then allowed to cool and the precipitated product was collected by filtration. The slightly yellow solid was washed with diethyl ether and dried under vacuum to provide the title compound (1.5 g, 86%), mp 262°–264° C (dec).

Analysis

Calculated for $C_{14}H_{14}IN_3O_2$: 43.88% C 8.68% H 10.97% N

Found: 1:3.77% C 3.58% H 10.96% N

EXAMPLE FIFTY-TWO

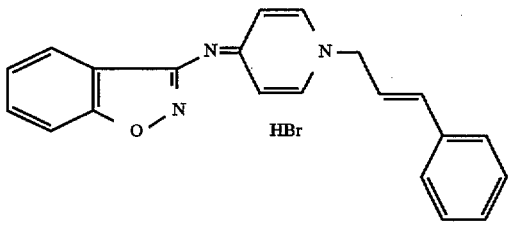

3-[1-(Trans-3-phenyl-2-propenyl)-N-4(1H)-pyridiniminyl]-1,2-benzisoxazole hydrobromide.

A mixture of 3-[(4-pyridinyl)amino]-1,2-benzisoxazole (1.0 g, 4.73 mmol) and cinnamyl bromide (0.93 g, 1 eq) in acetonitrile (25 mL) was heated at reflux for one hour. The mixture was then allowed to cool and the precipitated product was collected by filtration. The white solid was washed with diethyl ether and dried under vacuum to provide the title compound (1.8 g, 93%), mp 243°–244° C.

Analysis

Calculated for $C_{21}H_{18}BrN_3O$: 61.78% C 4.44% H 10.29% N

Found: 61.67C 4.27% H 10.:34% N

EXAMPLE FIFTY-THREE

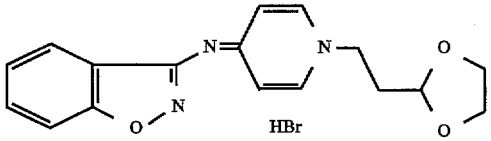

3-[1-[2-(1,3-dioxalane)ethyl]-N-4(1H)-pyridiniminyl]-1,2-benzisoxazole hydrobromide.

A mixture of 3o(4-pyridinylamino)-1,2-benzisoxazole (1.2 g, 5.7 mmol) and 2-(2-bromoethyl)-1,3-dioxolane (0.73 mL, 1.1 eq) in acetonitrile (25 mL) was heated to reflux for one hour. The mixture was then allowed to cool and the precipitate product was collected by filtration. The white solid was washed with diethyl ether and dried under vacuum to provide the title compound (0.95 g, 42%). The title compound was recrystallized from ethanol, mp 220°–221° C.

Analysis

Calculated for $C_{17}H_{18}BrN_3O_3$: 52.05% C 4.63% H 10.71% N

Found: 51.86C 4.51% H 10.52% N

EXAMPLE FIFTY-FOUR

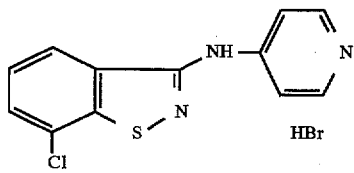

7-Chloro-3-[4-(pyridinyl)amino]-1,2-benzisothiazole.

4-Chloropyridine hydrochloride (2.2 eq) is added to 3-amino-7-chloro-1,2-benzisothiazole (1 eq) in N-methylpyrrolidone. The mixture is stirred at 130° C. for 1.5 hours. The resulting mixture is cooled, and then saturated sodium bicarbonate solution and water are added. The title compound is extracted into ethyl acetate, the combined organic extracts are washed with water, brine, dried over anhydrous magnesium sulfate, filtered and concentrated under vacuum. The residue is purified by column chromatography on silica gel to provide the title compound.

EXAMPLE FIFTY-FIVE

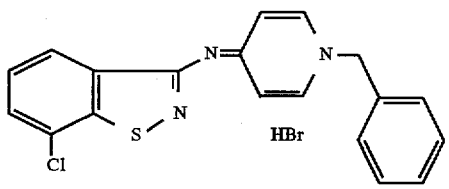

7-Chloro-3-[1-phenylmethyl-N-4(1H)-pyridiniminyl]-1,2-benzisothiazole hydrobromide.

7-Chloro-3-[4-(pyridinyl)amino]-1,2-benzisothiazole (1 eq) and benzyl bromide (1 eq) are combined in acetonitrile and heated at reflux for 1.5 hours. The mixture is then allowed to cool and the precipitated product is collected by filtration and dried under vacuum to provide the title compound.

REACTION SCHEME

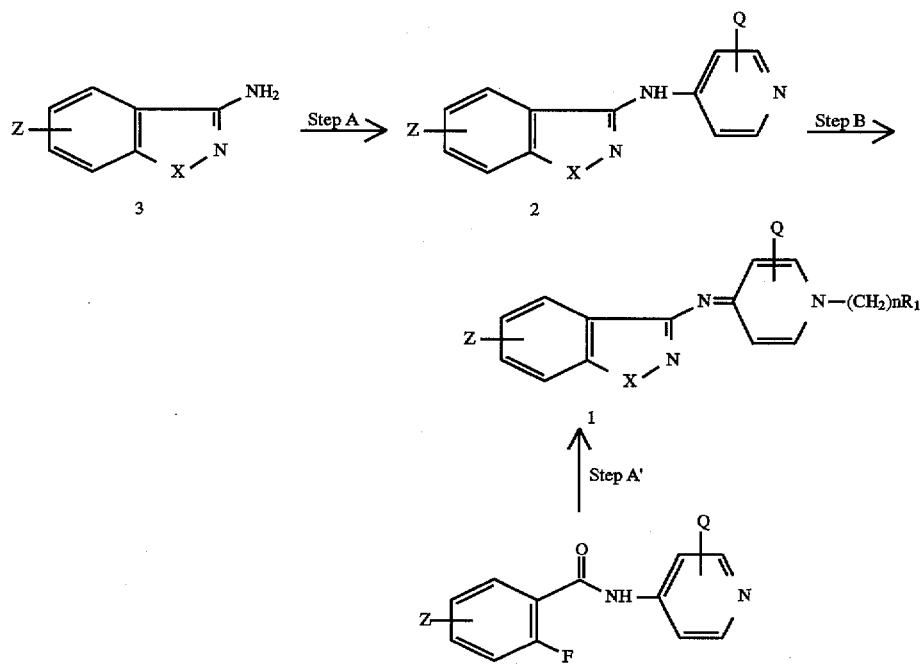

We claim:
1. A compound of the formula:

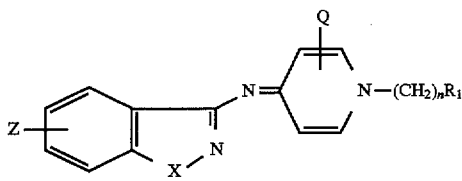

wherein $R_1$ is hydrogen, loweralkyl, loweralkenyl, loweralkynyl, lowercycloalkyl, —C(=O)O-loweralkyl, 1,3-dioxolane, phenyl, cinnamyl, phenyl substituted by loweralkyl, loweralkoxy, halogen, hydroxyl, nitro or trifluoromethyl; Q is hydrogen, halogen, loweralkyl or nitro; X is oxygen; Z is hydrogen, loweralkyl, loweralkoxy, hydroxyl, halogen, nitro, or trifluoromethyl; n is 1 to 12; the geometric isomers, the optical isomers, or the pharmaceutically acceptable salts thereof.

2. A compound according to claim 1 wherein $R_1$ is hydrogen, loweralkyl, loweralkenyl, loweralkynyl, lowercycloalkyl, phenyl, phenyl substituted by loweralkyl, loweralkoxy, halogen, hydroxyl, nitro or trifluoromethyl.

3. A compound according to claim 2 wherein X is oxygen and $R_1$ is hydrogen or loweralkyl.

4. A compound according to claim 2 wherein X is oxygen and $R_1$ is phenyl or phenyl substituted by loweralkyl, loweralkoxy, halogen, hydroxyl, nitro or trifluoromethyl.

5. A compound according to claim 2 which is 6-chloro-3-[1-propyl-N-4(1H)-pyridiniminyl]-1,2-benzisoxazote.

6. A compound according to claim 2 which is 3-[1-(4,4-dimethylpentyl-N-4(1H )-pyridiniminyl]-1,2-benzisoxazole.

7. A compound according to claim 2 which is 3-[1-(phenylmethyl)-N-4(1H)-pyridiniminyl]-1,2-benzisoxazole.

8. A compound according to claim 2 which is 3-[1-(2-phenylethy)l-N-4(1H)-pyridiniminyl]-1,2benzisoxazole.

9. A compound according to claim 2 which is 3-[1-(3-phenylpropyl)-N-(1H)-pyridiniminyl]-1,2-benzisoxazole.

10. A compound according to claim 2 which is 3-[1-(4-phenylbutyl)-N-(1H)-pyridiniminyl]-1,2-benzisoxazole.

11. A compound according to claim 2 which is 3-[1-(5-phenylpentyl)-N-(1H)-pyridiniminyl-1,2-benzis oxazole.

12. A compound according to claim 2 which is 3-[1-(2-methylphenyl)methyl-N-4(1H)-pyridiniminyl]-1,2-benzisoxazole.

13. A compound according to claim 2 which is 3-[1-(4-methylphenyl)methyl-N-4(1H)-pyridiniminyl]-1,2-benzisoxazole.

14. A compound according to claim 2 which is 3-[1-(3-methylphenyl)methyl-N-4(1H)-pyridiniminyl]-1,2-benzisoxazole.

15. A compound according to claim 2 which is 3-[1-(3-methoxyphenyl)methyl-N-4(1H)-pyridiniminyl]-1,2-benzisoxazole.

16. A compound according to claim 2 which is 3-[1-(3-fluorophenyl)methyl-N-4(1H)-pyridiniminyl]-1,2-benzisoxazole.

17. A compound according to claim 2 which is 3-[1-(2-fluorophenyl)methyl-N-4( 1H)-pyridiniminyl]-1,2-benzisoxazole.

18. A compound according to claim 2 which is 3-[1-(4-fluorophenyl)methyl-N-4(1H)-pyridiniminyl]-1,2-benzisoxazole.

19. A compound according to claim 2 which is 3-[1-(3-nitrophenyl)methyl-N-4(1H)-pyridiniminyl]-1,2-benzisoxazole.

20. A compound according to claim 2 which is 3-[1-(2-nitrophenyl)methyl-N-4(1H)-pyridiniminyl]-1,2-benzisoxazole.

21. A compound according to claim 2 which is 3-[1-(4-trifluormethylphenyl)methyl-N-4(1H)-pyridiniminyl]-1,2-benzisoxazole.

22. A compound according to claim 2 which is 3-[1-(3-trifluoromethylphenyl)methyl-N-4(1H)-pyridiniminyl]-1,2-benzisoxazole.

23. A compound according to claim 2 which is 5-fluoro-3-[1-phenylmethyl-N-4(1H)-pyridiniminyl]-1,2-benzisoxazole.

24. A compound according to claim 2 which is 6-methoxy-3-[1-phenylmethyl-N-4(1H)-pyridiniminyl]-1,2-benzisoxazole.

25. A compound according to claim 2 which is 6-nitro-3-[1-phenylmethyl-N-4(1H)-pyridiniminyl]-1,2-benzisoxazole.

26. A compound according to claim 2 which is 3-[1-(2-butynyl)-N-(1H)-pyridiniminyl]-1,2-benzisoxazole.

27. A compound which is 3-[1-(3-bromo-2-butenyl)-N-4(1H)-pyridiniminyl]-1,2-benzisoxazole.

28. A compound according to claim 2 which is 7-fluoro-3-[1-phenylmethyl-N-4(1H)-pyridiniminyl]-1,2-benzisoxazole.

29. A compound according to claim 2 which is 3-[1-(2-propenyl)-N-4(1H)-pyridiniminyl]-1,2-benzisoxazole.

30. A compound according to claim 2 which is 3-[1-(phenylmethyl)-N-(1H)-pyridiniminyl]-6-trifluoromethyl-1,2-benzisoxazole.

31. A compound according to claim 2 which is 3-[1-(phenylmethyl)-N-(1H)-pyridiniminyl]-5-trifluoromethyl-1,2-benzisoxazole.

32. A compound according to claim 2 which is 6-methoxy-3-[1-phenylmethyl-N-(1H)-3-bromopyridiniminyl]-1,2-benzisoxazole.

33. A compound according to claim 2 which is 6-fluoro-3-[1-phenylmethyl-N-(1H)-pyridiniminyl]-1,2-benzisoxazole.

34. A compound according to claim 2 which is 3-[1-phenylmethyl-N-4(1H)-pyridiniminyl]-7-trifluoromethyl-1,2-benzisoxazole.

35. A compound according to claim 2 which is 5-methoxy-3-[1-phenylmethyl-N-(1H)-pyridiniminyl]-1,2-benzisoxazole.

36. A compound according to claim 1 which is [4-(3-benzoisoxazolylimino)--(4H)-pyridinyl]-acetic acid methyl ester.

37. A compound according to claim 2 which is 7-methoxy-3-[1-phenylmethyl-N-(1H)-pyridiniminyl]-1,2-benzisoxazole.

38. A compound according to claim 2 which is 4-fluoro-3-[1-phenylmethyl-N-(1H)-pyridiniminyl]-1,2-benzisoxazole.

39. A compound according to claim 2 which is 6-fluoro-3-[1-methyl-N-4(1H)-pyridiniminyl]-1,2-benzisoxazole.

40. A compound according to claim 2 which is 6-methoxy-3-[1-methyl-N-4(1H)-pyridiniminyl]-1,2-benzisoxazole.

41. A compound according to claim 1 which is 3-[1-(trans-3-phenyl-2-propenyl)-N-4(1H)-pyridiniminyl]-1,2-benzisoxazole.

42. A compound according to claim 1 which is 3-[1-[2-(1,3-dioxalane)ethyl]-N-(1)-pyridiniminyl]-1,2-benzisoxazole.

43. A memory dysfunction relieving composition comprising an adjuvant and as the active ingredient, a memory dysfunction relieving effective amount of a compound of claim 1.

44. A method of relieving memory dysfunction in mammals comprising administering to a mammal requiring memory dysfunction relief, a memory dysfunction relieving effective amount of a compound of claim 1.

* * * * *